United States Patent
Renimel et al.

(12) 
(10) Patent No.: US 6,676,952 B2
(45) Date of Patent: *Jan. 13, 2004

(54) USE OF AN OKUME RESIN EXTRACT IN THE COSMETIC AND PHARMACEUTICAL FIELDS, AND IN PARTICULAR IN THE DERMATOLOGICAL FIELD

(75) Inventors: Isabelle Renimel, Trainou (FR); Patrice Andre, Neuville Aux Bois (FR)

(73) Assignee: Parfums Christian Dior, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,854
(22) PCT Filed: Dec. 15, 1997
(86) PCT No.: PCT/FR97/02296
§ 371 (c)(1), (2), (4) Date: Jun. 11, 1999
(87) PCT Pub. No.: WO98/26750
PCT Pub. Date: Jun. 25, 1998

(65) Prior Publication Data
US 2002/0006416 A1 Jan. 17, 2002

(30) Foreign Application Priority Data
Dec. 16, 1996 (FR) .............................. 96 15448

(51) Int. Cl.[7] .............. A61K 6/00; A61K 7/42; A61K 7/04; A61K 7/06; A61K 7/035
(52) U.S. Cl. .......... 424/401; 424/59; 424/61; 424/69; 424/707; 424/419
(58) Field of Search ................. 424/401, 419, 424/59, 61, 69, 70.7

(56) References Cited

U.S. PATENT DOCUMENTS

| | | | | |
|---|---|---|---|---|
| 4,056,400 A | * | 11/1977 | Diamantoglou et al. | 106/162 |
| 5,422,100 A | * | 6/1995 | Eliaz et al. | 424/70.1 |
| 5,554,596 A | * | 9/1996 | Mach, et al. | 514/22 |
| 5,965,183 A | * | 10/1999 | Hartal et al. | 426/250 |
| 5,972,341 A | * | 10/1999 | Andre et al. | 424/195.1 |
| 6,203,782 B1 | * | 3/2001 | Eliaz et al. | 424/70.1 |

FOREIGN PATENT DOCUMENTS

| | | | | |
|---|---|---|---|---|
| JP | 405178755 A | * | 7/1993 | |
| WO | 96/13178 | * | 5/1996 | |

OTHER PUBLICATIONS

STN, Data base server XP002033673 Karlsruhe, DE, File Chemical Abstracts, Vol 93, AN=197959, Abstract.
STN, Data base server XP002033675, Karlsruhe, DE, File Chemical Abstracts, vol 110, AN=92005 Abstract.

* cited by examiner

Primary Examiner—Thurman K. Page
Assistant Examiner—S. Tran
(74) Attorney, Agent, or Firm—Merchant & Gould P.C.

(57) ABSTRACT

The invention relates to novel uses of an extract of okume resin in the cosmetic and pharmaceutical fields, and in particular in the dermatological field. It relates to cosmetic compositions for treating the nails, the hair, or the eyelashes in order to maintain their keratin structure in good condition, for combatting aging of the skin, for combatting the harmful effects of free radicals, and for the care or makeup of sensitive skin. It also relates to dermatological compositions, more particularly compositions for preventing or treating diseases of the hair or the nails.

13 Claims, 2 Drawing Sheets

USE OF AN OKUME RESIN EXTRACT IN THE COSMETIC AND PHARMACEUTICAL FIELDS, AND IN PARTICULAR IN THE DERMATOLOGICAL FIELD

This application is a 371 of PCT/FR 97/02296 filed Dec. 15, 1997.

The invention relates to novel uses of an okume resin extract, in the cosmetic and pharmaceutical fields, and in particular in the dermatological field.

More precisely, the invention relates to uses as a cosmetic agent of an okume resin extract, more particularly for care of the skin, the nails, and the hair.

The invention also relates to certain uses in the field of pharmacy.

"Okume" and "Gaboon mahogany" are common names corresponding to the plant *Aucoumea klaineana* which is the only species of the genus Aucoumea of the family Burseraceae.

The okume is a tall tree of the equatorial rain forests of West and Central Africa. It is used for its wood and constitutes the majority of the wood exported by Gabon.

Its young branches are covered in rust-red down. Its leaves are alternate, imparipinnate, and with elongate oval leaflets, and they are glabrous and shiny. Young leaves are a bright red color; they appear starting in October to December-January, giving the tree tops a reddish color, which makes it possible to identify okume populations from the air.

The inflorescences are in 10 cm to 20 cm long panicles, with whitish flowers that are practically odorless. Flowering takes place in October-November.

The fruit are capsular and glabrous; they open into five leathery lobes. The seeds are triangular, and extended by a blade-shaped wing. Fruiting is towards the month of February.

The color of the bark varies from purplish red to salmon pink depending on the age of the plant. The bark is lightly fibrous, almost granulous, and when cut it oozes out a resin or oleoresin that smells strongly of turpentine and that becomes opaque on coagulating.

The resin essentially contains monoterpenes and triterpenes with a backbone of olenane and tirucallane.

Traditional uses are known for this resin: originally okume resin was used in Gabon to make torches used during initiation ceremonies. That use which persists to the present day in villages, is extended in towns during family gatherings. In missionary stations, it is used as a substitute for incense. In folk medicine, it is used to bring abscesses to a head and in the treatment of wounds where it activates healing.

Pharmacologically, the oleoresin has antibacterial power, due in particular to phenols contained in essential oil.

For further details on the uses and properties of okume or its oleoresin, reference can be made to the following publications:

Tessier A. M., Delaveau P., Piffault N., Hoffelt J., Planta Med. 46, 41 (1982);

Delaveau P., Lallouette P., Tessier A. M., Planta Med., 40, 49 (1980);

Delaveau P., Vidal-Tessier A. M., Bull. Soc. Bot. Fr., 135, Actualités bot., 3, 25 (1988).

Systemic testing carried out by the inventors has revealed a certain number of surprising enzymatic actions of this resin, in particular inhibiting action on various enzymes, in particular keratinase, elastase, phospholipase $A_2$, and lipoxygenase, which makes it possible to envisage using it in cosmetics, in particular in substances for care of the skin, the nails, and the hair.

Keratinase is an enzyme produced on the body essentially by fungi. It is produced industrially from *Streptomyces fradiae*. Its action on the skin, and on the integuments leads to degradation of keratins, which gives rise in particular to disorganization in the structure of the integuments (white or striped nails, brittle hair, etc.).

Elastase, the enzyme for degrading elastin, is present in cells, in particular in dermal cells (fibroblasts) and also, to a lesser extent, in epidermal cells (keratinocytes). It has been observed that the quantity and the activity of elastase increases during the process of skin aging, whether the aging is intrinsic or actinic. By degrading elastin fibers, the action of elastase causes a loss of cutaneous elasticity, a slackening of the skin, and the appearance of wrinkles.

Phospholipase $A_2$ ($PLA_2$) is an enzyme produced by membrane cells. It predominates in cells associated with inflammatory phenomena, such as mast cells. Its action is to release arachidonic acid bonded to the phospholipids of the membrane. This acid then metabolizes into various lipid mediators of inflammation and allergy, such as leukotrienes and prostaglandins.

5'-lipoxygenase, referred to below as "lipoxygenase" is, like $PLA_2$, a membrane enzyme. It is involved in the "inflammation cascade" downstream from the release of arachidonic acid by $PLA_2$, in converting the acid into leukotrienes, mediators of inflammation.

The inventors have thus shown that because of their inhibiting action on the above-mentioned enzymes, extracts of okume resin are most advantageous in cosmetics and in therapy.

More particularly, the invention provides compositions for care of the nails, the hair, and the eyelashes, in combatting the effects of skin aging, and in preventing or treating cutaneous inflammations and allergies.

By the discovery that okume resin extracts are active in inhibiting the action of enzymes, the invention provides various solutions in the field of cosmetics and therapy, and in particular in the field of dermatology. By inhibiting keratinase, the compositions of the invention serve to prevent and treat deterioration of keratin structures, in particular in the integuments, the nails, the hair, and eyelashes. By inhibiting elastase, the compositions of the invention oppose degradation of elastin fibers, and as a result such compositions maintain the biomechanical qualities of the skin, and in particular its qualities of elasticity in the dermis, thus combatting slackening of the skin and the appearance of wrinkles. By inhibiting phospholipase $A_2$ and lipoxygenase, compositions of the invention thus have two actions in limiting or blocking the process of forming cutaneous allergy mediators and inflammation mediators.

In another advantage of the invention, okume resin turns out to be soluble in numerous organic solvents. It is even almost completely soluble in esters such as ethyl acetate and butyl acetate, thus making it all the more advantageous in the manufacture of nail varnish, which generally makes use of these solvents, in particular in the manufacture of treatment nail varnish.

Another advantage of using okume resin extracts in treatments for the nails, in particular in nail varnishes, stems from the fact that these extracts themselves have film-forming characteristics when applied on a surface, in particular the surface of a nail.

These film-forming qualities of okume resin can also be used to advantage in compositions for application to the hair or to the eyelashes, in particular in compositions for hair dressing such as lacquers, gels, or emulsions, or indeed in mascara compositions for improving the coating of eyelashes.

Other advantages of the invention appear from the following description and examples.

Thus, according to one of its essential characteristics, the invention relates to cosmetic compositions containing an okume resin extract in the presence of a cosmetically acceptable vehicle.

The extract is advantageously obtained by macerating the resin in a solvent of medium or weak polarity, followed by filtering the mixture. The solvent of the resulting solution can be evaporated where necessary in order to obtain a dry extract.

A solvent of "medium or weak polarity" means a solvent whose polarity parameter is less than or equal to 6, where this index is defined in Practical high-performance liquid chromatography by Meyer V. R., 1988, pp. 120–121.

Evaporation is preferably performed under low pressure.

Solvents that can be used advantageously include the following:

$C_6$ to $C_{12}$ aliphatic hydrocarbons such as hexane and heptane;

chlorine-containing solvents, in particular dichloromethane;

ethers such as ethyl ether or diisopropyl ether;

acetone;

esters such as ethyl acetate and butyl acetate; and $C_1$ to $C_4$ alcohols, such as methanol, ethanol, and isopropanol.

Okume resin extract can also be obtained by the so-called supercritical carbon dioxide extraction technique.

Extraction yield depends essentially on the age of the tree.

Thus, by using ethyl acetate as the solvent, extraction yield lies in the range 90% to 98% depending on the age of the tree.

In an advantageous embodiment, the composition comprises 0.01% to 10% by weight and in particular 0.2% to 1% by weight dry extract of okume resin relative to the total weight of the final composition.

In other advantageous embodiments of the invention, the composition is formulated for topical application to the skin, to the hair, to the eyelashes, or to the nails.

Tests performed by the inventors have also clearly shown that not only is extraction yield tied to the nature of the solvent used, but so also is the enzymatic activity of the extract. The accompanying examples show clearly the effect of solvent selection on the enzymatic activity of the extract.

The quantity of extract is also selected as a function of the desired film-forming effect. A particular advantage associated with the nature of the substance enables the extract to confer film-forming qualities to the composition, or to improve them.

Compositions of the invention can be formulated in any form that is accepted for their use in cosmetics. In particular, the composition can be a cream, in particular a cream for the face or the hands, a gel, in particular a hair gel, a balm, in particular untangling balm, a mascara, a foundation, or a preparation for the nails, such as a treatment base or a treatment nail varnish.

In another aspect, the invention concerns the use of okume resin as a cosmetic agent, said agent being incorporated in a cosmetic composition as defined above.

The quantity of this agent can be adapted as a function in particular of the film-forming qualities desired of the composition.

Cosmetic compositions of the invention are used in any field associated with care or makeup.

In particular, the cosmetic agent can be used in all applications where it is desired to inhibit the action of keratinase and/or elastase and/or phospholipase $A_2$ and/or lipoxygenase.

Such compositions are intended in particular for care of the nails, the hair, or the eyelashes, in particular for keeping them in good condition as to keratin structure, so as to facilitate hair dressing or to improve eyelash makeup.

Such compositions are also used to combat the effects of skin aging, in particular by preserving or improving the biomechanical qualities of the skin, in particular its elasticity, by delaying the appearance of wrinkles, or by reducing wrinkle depth and improving cutaneous firmness.

Such compositions are also used for combatting the harmful effects of free radicals on the skin, for care or makeup of sensitive skins, in particular by attenuating or eliminating phenomena of irritation, inflammation, or allergy that generally give rise on the skin to red patches, or to burning or tingling sensations.

Thus, cosmetic compositions of the invention are used in particular for any cosmetic application where it is desired to inhibit the activity of the above-mentioned enzymes.

This is the case in particular of compositions for care of the hair, the eyelashes, or the nails, where said antikeratinase activity is particularly desired.

Thus, in another aspect, the invention relates to cosmetic compositions for care of the skin, in particular to combat inflammation or cutaneous aging.

In yet another aspect of the invention, it provides cosmetic compositions for hair care. In particular, they can be hair lacquers, gels, or emulsions.

The invention also provides makeup, in particular treatment makeup such as nail varnishes, mascaras, or foundations.

In a particularly advantageous aspect of the invention, it also relates to cosmetic compositions for treatment of the nails. Keratin, a structural protein, is predominant in nails and imparts rigidity thereto. With aging, keratins become less rigid, so nails become softer, more breakable, and also more vulnerable to attack from various proteases such as keratinase. Compositions of the invention can thus advantageously be used for nail care, in particular because of their keratinase inhibition action as demonstrated by tests performed by the inventors.

In addition to its properties of inhibiting keratinase and its quasi-total solubility in the solvents used for preparing nail varnishes, okume resin has the advantage of improving the film-forming character of such compositions, thus greatly contributing to the Theological properties and qualities of such varnishes after they have been applied to the nails.

As mentioned above, the effectiveness of the above-described cosmetic compositions has been correlated with various kinds of enzymatic activity. The demonstration of this enzymatic activity makes it possible also to envisage using the above-defined extracts for preparing pharmaceutical compositions, in particular dermatological compositions in which these kinds of activity are desired. Tests performed by the inventors of the present invention have confirmed the effectiveness of such pharmaceutical compositions.

Thus, phospholipase $A_2$ inhibition and 5'-lipoxygenase inhibition have been correlated with effectiveness in preventing and treating inflammation phenomena.

In addition, keratinase inhibition activity has been correlated with activity in the field of treating complaints affecting keratin, in particular in the nails, the eyelashes, and the hair.

Thus, according to another essential characteristic, the invention also provides the use of an okume resin extract in preparing a pharmaceutical composition, in particular a dermatological composition, for preventing or treating complaints of the integuments, in particular the nails, giving rise to deterioration of keratin structures, such as onychomycoses, for treating the effects of intrinsic or actinic aging of the skin, for treating the harmful effects of free radicals on the skin, for preventing or treating cutaneous manifestations of allergies and inflammations, said extract being incorporated in a pharmaceutically acceptable vehicle.

The invention also relates to methods of therapeutic and in particular dermatological treatment, for preventing or treating complaints of the integuments, in particular the nails, giving rise to deterioration of keratin structures, such as onychomycoses, for treating the effects of intrinsic or actinic aging of the skin, for treating the harmful effects of free radicals on the skin, for preventing or treating cutaneous manifestations of allergies and inflammations, in which an effective quantity of a pharmaceutical composition containing an okume resin extract is applied to the part of the body to be treated.

For these various applications, the pharmaceutical composition advantageously presents inhibitory activity on keratinase and/or elastase and/or phospholipase $A_2$ and/or lipoxygenase.

In a variant, the invention relates to using an okume resin extract for preparing a pharmaceutical composition, in particular a dermatological composition, for treating and preventing manifestations of allergies, in particular cutaneous allergy or the treatment of the harmful effects of free radicals.

These two types of application are directly associated with inhibiting the lipid mediators of inflammation.

In these applications in the pharmaceutical field, in particular in the dermatological field, the compositions used are preferably compositions for topical application designed to be applied in particular to the skin and the integuments. The okume resin extracts used for preparing them are obtained in the same manner as the extracts used in the field of cosmetics, and they are introduced into a vehicle that is pharmaceutically and in particularly dermatologically acceptable in concentrations lying in the range 0.01% to 10% by weight, and in particular in the range 0.2% to 1% by weight, of dry extract of said resin.

As in cosmetic applications, the extraction solvent is selected as a function of the type of enzymatic activity that it is desired to favor in the action of the pharmaceutical composition.

Pharmaceutical, and in particular dermatological, compositions of the invention can also contain various pharmacologically active substances usable in the treatment of diseases of the integuments and in particular of the nails.

In particular, such compositions can contain agents known for their antifungal activity, in particular agents that are active on the dermatophytes that are responsible in particular for onychomycoses.

Amongst these agents, particular mention can be made of the ethanolamine salt of ciclopirox, also known as ciclopirox olamine.

The following examples are given purely to illustrate the invention. With reference to the examples, there are also given FIGS. 1 to 4, in which, respectively:

Figure 1:
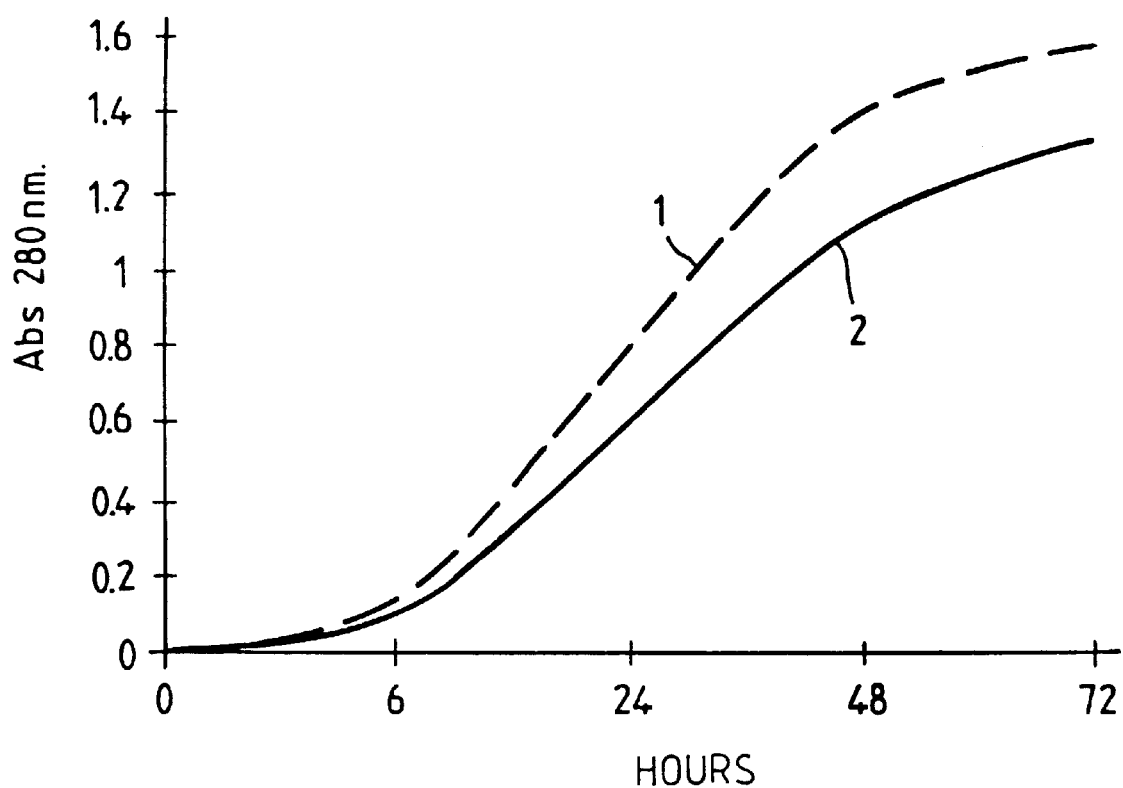
FIG. 1 shows how absorbance at 280 nm varies as a function of time in the presence of a reaction medium containing keratinase and nail clippings in the presence of (curve 1) and in the absence of (curve 2) okume resin. This figure is given with reference to Example 3.

Unless otherwise stated, the proportions given in the example compositions are expressed in percentage by weight.

EXAMPLE 1

Preparing an Extract of Okume Oleoresin of the Invention 100 grams (g) of previously-ground oleoresin were introduced into 1000 milliliters (ml) of ethyl acetate. The suspension was left at ambient temperature under moderate stirring for 3 hours. Thereafter the mixture was filtered and then the solvent was evaporated from the resulting filtrate under reduced pressure. About 95 g of dry extract of okume resin were then obtained having the appearance of a syrupy residue. To prepare the compositions of the invention, it is possible to use either the solution of resin extract in the extraction solvent and optionally concentrated, or else to use the dry extract. Thus, to prepare the nail varnish of the invention, it is possible to use a solution of the resin in ethyl acetate or in butyl acetate. For example, it is possible to use a solution having 10% resin extract.

EXAMPLE 2

Demonstrating the Inhibitory Activity of Okume Oleoresin on Various Enzymes 2.1 Extracts Used Since the enzyme inhibition tests were performed in an aqueous medium, it was necessary to use extraction solvents that are miscible in water.

Thus, proceeding as described in Example 1, but using other solvents, three different extracts were prepared respectively with water, with methanol, and with dimethyl sulfoxide (DMSO). The concentration of the extracts was then adjusted to 0.5% dry extract of resin, either by adding or by evaporating the extraction solvent.

All of the tests described below were performed in triplicate. The values given are arithmetical means.

2.2 Inhibition of Elastase a) Principles of the Test

The techniques for demonstrating elastase inhibition has been described by various authors (Baumstark J. S. et al., Biochim. Biophys. Acta (1963), 77, 676: Bieth B. et al., Biochem. Med. (1974), 11, 350; Franck C., Bryjalsen I., Biol. Chem. Hoppe Seyler (1988) 369 (8), 677–682).

The active principle is as follows: a substrate is put into the presence of elastase in an aqueous medium, and then after incubation, the reaction products are measured.

Specifically, the substrate is N-succinyl-(Ala)$_3$-para-nitroanilide, available from Sigma (ref. S4760) in solution at 0.5 milligrams per milliliter (mg/ml) in a 0.2 M Tris-HCl buffer at a pH of 8.8. The elastase added to the reaction medium releases para-nitroaniline and the peptide residue. Progress of the reaction was observed on a Uvikon 941® spectrophotometer (from Kontron S. A.) at a wavelength λ of 379 nanometers (nm).

The composition of the reaction medium was as follows:

| | |
|---|---|
| substrate solution (0.5 mg/ml of buffer): | 200 µl |
| Tris-HCl buffer: | 600 µl |
| extraction solvent: | 100 µl |

The extraction solvent either did or did not contain the effector, i.e. the extract of okume resin, at a concentration of 0.5% by weight, depending on whether the test was with effector or without effector (baseline activity of the enzyme).

100 µl of enzyme solution at a concentration of 35 U/ml in the Tris-HCl buffer were added to the 900 µl of reaction medium.

The kinetics of para-nitroaniline release were measured by the absorption of monochromatic light at a wavelength of 379 nm by means of the spectrophotometer, thus making it possible to calculate the inhibition percentage $I_E$ using the following equation:

$$I_E = \frac{\Delta AbB/\min - \Delta AbE/\min}{\Delta AbB/\min} \times 100$$

in which ΔAbB/min is the difference per minute in the absorbance of the reaction medium for baseline activity, and ΔAbE/min is the absorbance difference of the reaction medium for the test with the effector. The results are given in Table I below.

2.3 Inhibition of Phospholipase $A_2$

This test is based on the principle of putting the enzyme into the presence of a phospholipid (Uthe J. F. and Magee W. L., Can. J. Biochem. (1971), 49, 776: Dennis E. A., J. Lipids Res. (1973), 14, 152). The phospholipid is then transformed into lysolecithin with release of a fatty acid that is insoluble in the reaction medium. The reaction can then be tracked by turbidimetry by means of a spectrophotometer, e.g. using a wavelength of 360 nm.

The composition of the reaction medium was as given below. All of the solutions were made using distilled water.

| | |
|---|---|
| solution having 14 mM of L-phosphatidylcholine dimyristoyl (substrate): | 600 µl |
| 0.67 M solution of sodium chloride: | 150 µl |
| 66 mM solution of calcium chloride: | 200 µl |
| distilled water: | 850 µl |
| solvent with or without effector at 0.5%: | 100 µl |

100 µl of enzyme solution in distilled water at a concentration of 96 U/ml were added to the above medium.

As with elastase inhibition, the reaction kinetics were tracked by means of a Uvikon 941® spectrophotometer, at the wavelength of 360 nm.

The inhibition percentage $I_p$ of phospholipase $A_2$ was determined by calculation using an equation analogous to that used for elastase inhibition:

$$I_p = \frac{\Delta AbB/\min - \Delta AbE/\min}{\Delta AbB/\min} \times 100$$

in which ΔAbB and ΔAbE have the same meanings as above.

The results are given in Table I below.

2.4 Inhibition of 5'-lipoxygenase

As already explained above lipoxygenase takes part in the formation of inflammation mediators, in particular leukotrienes, starting from arachidonic acid.

In the test for showing inhibition of this enzyme (Taylor C. W., Morris H. R., Brit. Med. Bull. (1989), 39, 219–222; Magee J., Methods of Enzymatic Analysis, H. U. Bergmayer Ed. (1965), pp. 411–414, Academic Press, NY), linoleic acid used as the substrate and it is transformed in the presence of the enzyme into 5-hydroperoxy-6,8,11,14-eicosatetraeonic (5 HPETE) acid.

Composition of the reaction medium:

| | |
|---|---|
| 0.5 mM solution of linoleic acid (substrate) | 2000 µl |
| 0.2 M borate buffer at pH 9: | 950 µl |
| solvent with or without effector at 0.5% in the borate buffer: | 100 µl |

To prepare the above linoleic acid solution, linoleic acid was initially subjected to partial salification in methanol in the presence of sodium hydroxide, and then it was introduced into the borate buffer.

Thereafter 100 µl of the solution of 5'-lipoxygenase enzyme in the borate buffer at a concentration of 10 U/ml was added.

As in the preceding tests, the absorbances of the media were measured as a function of time, and the inhibition percentage $I_L$ of 5'-lipoxygenase was calculated.

The results appear in Table I below.

TABLE I

| | Enzyme inhibition rates | | |
|---|---|---|---|
| | elastase $I_E$ | phospholipase $A_2$ $I_P$ | 5'-lipoxygenase $I_L$ |
| $E_E$ | 17% | 25% | 18% |
| $E_M$ | 72% | 22% | 32% |
| $E_D$ | 75% | 43% | 61% |

$E_E$: aqueous extract of okume oleoresin at 0.5% in water (solvent).
$E_M$: methanolic extract of okume oleoresin at 0.5% in methanol (solvent).
$E_D$: extract of okume oleoresin in DMSO at 0.5% in the DMSO (solvent).

The inhibition results obtained can be considered as being significant for inhibition values greater than 25%.

The fraction of okume resin extracted by DMSO has very significant inhibitory activity on all three enzymes. The methanolic fraction presents inhibitory activity equivalent to that of the DMSO fraction on elastase, and significant inhibitory activity on 5'-lipoxygenase. However this fraction is of very low activity for inhibiting $PLA_2$. The aqueous fraction presents very low inhibitory activity on all three enzymes tested.

It must be concluded from these experimental results that the active principles present in okume resin and extracted by the organic solvents tested are not extracted by solvents that are too polar, such as water.

These results show the advantage of okume resin extracts of the invention in the fields of cosmetics and pharmacy, particularly dermatology, whenever there is a question of combatting the unwanted effects due to the action of these enzymes.

EXAMPLE 3

Protection of Ungual Keratin 500 mg of nail clippings were put into the presence of keratinase with or without extract of okume resin for 3 days under stirring at 37° C. Samples were taken for measuring the proteins at 6, 12, 24, 48, and 72 hours, and the proteins released were measured by measuring absorbents. In these steps, the okume resin extract was made as in Example 1, and was used in 1% solution in ethyl acetate.

Table 2 below gives the compositions of the reaction media for the tests performed.

The buffer solution used was a 0.1 M Tris-HCl buffer solution with a pH of 7.5. The concentration of the enzyme solutions in the buffer was 480 U/ml. The enzyme was deactivated by heating to 100° C. for 10 min.

It should be observed that a "blank enzyme" test, i.e. with the enzyme deactivated, was necessary to take account of the absorbance at 280 nm associated with merely adding the enzyme.

TABLE 2

|  | Blank enzyme | Baseline activity | Okume treatment |
|---|---|---|---|
| Nail (mg) | 500 | 500 | 500 |
| Deactivated enzyme | 100 μl | — | — |
| Active enzyme | — | 100 μl | 100 μl |
| Ethyl acetate | 200 μl | 200 μl | — |
| Solution of okume extract | — | — | 200 μl |
| Buffer | 1 ml | 1 ml | 1 ml |

The quantity of proteins released into the reactive medium was proportional to the absorbance measured at 280 nm by means of a Uvikon 941® spectrophotometer. The results of absorbance measurements are given in FIG. 1 where the dashed line curve (curve 1) corresponds to absorbance in the presence of keratinase on its own, while the solid line curve (curve 2) corresponds to absorbance in the presence of keratinase and okume extract. At 24 hours, the absorbance of the medium containing the okume extract was 12% less than that of the reference medium (baseline activity). At 48 h, the inhibition was 25%, and it then stabilized at about 28% as from 72 h. It can clearly be seen from these results that the presence of okume resin extract inhibits the action of keratinase, thus protecting ungual keratin.

EXAMPLE 4
Demonstrating the Film-forming Effect

Figure 2:
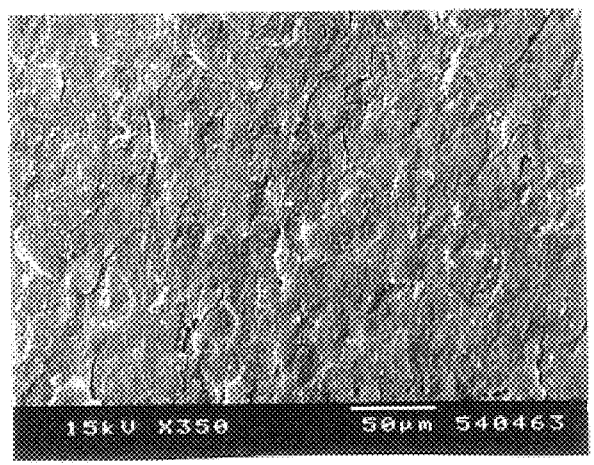
FIG. 2 is a photograph from an electron microscope at a magnification of ×350 of an untreated nail.
Figure 3:
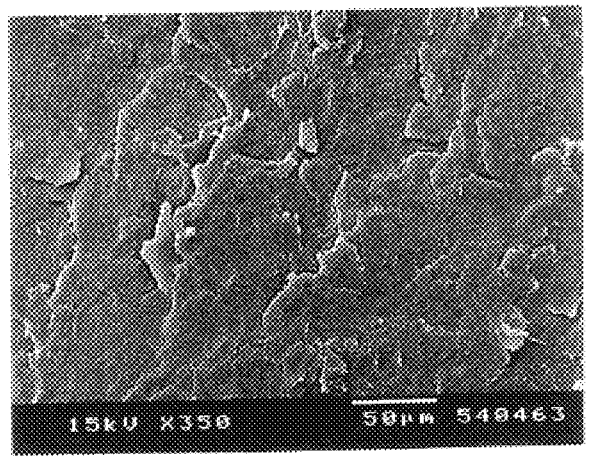
FIG. 3 is a photograph from an electron microscope at a magnification of ×350 of a nail after 48 hours (h) of treatment with keratinase.
Figure 4:
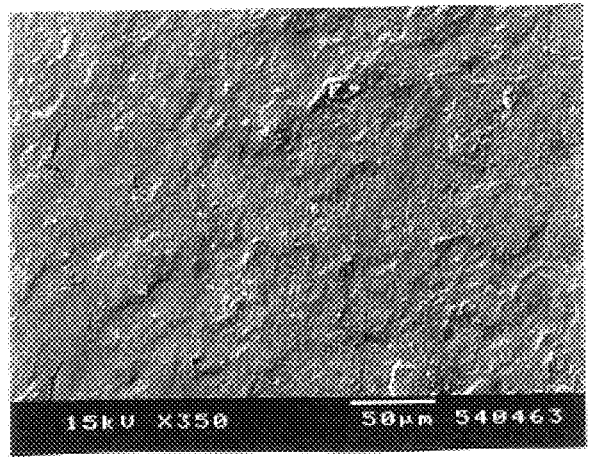
FIG. 4 is a photograph from an electron microscope at a magnification of ×350 of a nail after the same treatment as in the case of FIG. 3, but in the presence also of extract of okume resin.

Observations were made by electron microscope on pieces of nail after they had been in contact for 48 h with the reaction media of the above-described keratinase inhibition test, and these observations serve to show the differences between a reference nail, and nails exposed to keratinase both with and without okume protection treatment. These results can be seen clearly in the photographs made by an electron microscope firstly of a reference nail (FIG. 2), secondly of a nail treated with keratinase (FIG. 3), and thirdly of a nail treated with keratinase in the presence of okume resin (FIG. 4). In the photographs, it can be seen clearly that not only does the presence of okume resin protect the nail from being attacked by keratinase, but also that it leads to a film-forming effect which gives rise to the nail having an appearance of greater smoothness.

EXAMPLE 5

| Dermatological ointment for the nails | |
|---|---|
| Dry extract of okume resin from Example 1: | 0.5 g |
| Fatty excipient (polyoxyethylene fatty alcohols, glycerol, inter-esterified maize oil, lauryl trihydroxy-3,4,5-benzoate, a mixture of sorbitol and polyglycol stearate, purified water): | qsp 100 g |

This ointment can be applied morning and evening to damaged nails, in particular as a treatment accompanying anti-mycotic treatment.

EXAMPLE 6

| Dermatological cream for the nails | |
|---|---|
| Dry extract of okume resin from Example 1: | 1.0 g |
| Ciclopirox ethanolamine salt: | 1.0 g |
| Oil-in-water emulsified excipient: | qsp 100 g |

This cream associating an okume resin extract and an antifungal agent is most advantageous in treating dermatophyte onychomycoses.

EXAMPLE 7

| Antiwrinkle cosmetic gel | |
|---|---|
| Dry extract of okume resin, methanolic fraction from Example 2: | 0.05 g |
| Carbomer: | 0.3 g |
| Glycerin: | 3.0 g |
| EDTA tetarsodium: | 0.05 g |
| Aqueous extract of witch hazel: | 3.00 g |
| Polymethylmethacrylate: | 1.00 g |
| Perfumes, preservatives, coloring, neutralizers: | qs |
| Distilled water: | qsp 100 g |

This gel has an antiwrinkle and soothing effect.

This gel has an antiwrinkle and soothing effect.

EXAMPLE 8

| Untangling balm, to be rinsed | |
|---|---|
| Dry extract of okume resin from Example 1: | 1.0 g |
| Cetostearyl alcohol + cetearyl glucoside: | 5.0 g |
| Quaternium - 82: | 2.0 g |
| Cocamidopropyl betaine: | 3.0 g |
| Neutralizer: | qsp pH 5.5 |
| Perfumes, preservative, coloring: | qs |
| Water: | qsp 100 g |

EXAMPLE 9

| Antiwrinkle cream for the face | |
|---|---|
| Dry extract of okume resin from Example 1: | 0.5 g |
| Glyceryl stearate + PEG 100 stearate: | 5.0 g |
| Cetyl alcohol | 1.0 g |
| Stearyl alcohol: | 1.0 g |
| Beeswax: | 1.50 g |
| Squalane: | 3.0 g |
| Hydrogenated polyisobutene: | 4.0 g |
| Cetearyl octanoate: | 1.50 g |
| Tricaprylate/caprate of glycerol: | 3.0 g |
| Dimethicone: | 1.0 g |
| Xanthan gum: | 0.2 g |
| Carbomer: | 0.15 g |

-continued

Antiwrinkle cream for the face

| | |
|---|---|
| Glycerin: | 2.0 g |
| Neutralizer, preservative, perfumes, coloring: | qs |
| Water: | qsp 100 g |

EXAMPLE 10

Cream for sensitive skin

| | |
|---|---|
| Dry extract of okume resin, methanol fraction of Example 2: | 0.2 g |
| Methylglucose sesquistearate: | 3.0 g |
| Beeswax: | 3.0 g |
| Behenyl alcohol: | 3.0 g |
| Octyl octanoate: | 5.0 g |
| Fluid mineral oil: | 7.5 g |
| Cetostearyl ocanoate: | 5.0 g |
| Glycerin: | 3.0 g |
| Xanthan gum: | 0.50 g |
| Perfumes: | 0.30 g |
| Preservative, coloring: | qs |
| Water: | qsp 100 g |

EXAMPLE 11

Treatment base for nails

| | |
|---|---|
| Dry extract of okume resin at 10% in ethyl acetate, from Example 1: | 10 |
| Ethyl acetate: | 20.5 |
| Butyl acetate: | 30.5 |
| Arylsulfonamide resin: | 9.1 |
| Camphor: | 1.9 |
| 70% nitrocellulose in isopropanol: | 18.5 |
| Dibutylphthalate: | 5.5 |
| Steralkonium hectorite: | 1.3 |
| 10% citric acid solution in isopropanol: | 0.6 |
| Isopropranol: | 2.1 |

EXAMPLE 12

Treatment nail varnish

| | |
|---|---|
| Dry extract of okume resin at 10% in ethyl acetate from Example 1: | 20 |
| Ethyl acetate: | 10 |
| Butyl acetate: | 30 |
| Polyester resin: | 9.1 |
| Camphor: | 1.9 |
| 70% nitrocellulose in isopropanol: | 18.5 |
| Dibutylphthalate: | 5.5 |
| Stearalkonium hectorite: | 1.3 |
| 10% citric acid solution in isopropranol: | 0.6 |
| Isopropanol: | 2.1 |
| Pigments: | 1 |

What is claimed is:

1. A cosmetic composition comprising an extract of okume resin in the presence of a cosmetically acceptable vehicle, wherein the extract is obtained by maceration of said resin in a solvent or a mixture of solvents having a poladty parameter that is less than or equal to 6 and subsequent filtering of said maccrated resin, wherein said composition is presented in the form of a cream, a gel, a balm, a mascara, a foundation, or a preparation for the nails.

2. The composition according to claim 1, wherein said solvent is selected from the group consisting of $C_6$ to $C_{12}$ aliphatic hydrocarbons, chlorine-containing solvents, ethers, acetone, esters, and $C_1$ to $C_4$ alcohols.

3. The composition according to claim 1, wherein said extract comprises 0.01% to 10% by weight dry extract of said resin.

4. A method of cosmetic treatment comprising application to the skin, the nails, the hair, or the eyelashes of a cosmetic composition as defined in claim 1.

5. The method according to claim 4, wherein said composition is a care or makeup composition.

6. The method according to claim 4, wherein said method is for delaying or lowering the effects of the aging on the skin.

7. The method according to claim 4, wherein said method is selected from a group consisting of a method for counteracting the harmful effects of free radicals on the skin, a method for treating sensitive skins and making up sensitive skins.

8. A cosmetic composition comprising an extract of okume resin in the presence of a cosmetically acceptable vehicle, wherein said extract is obtained by supercritical carbon dioxide extraction, and wherein said composition is presented in the form of a cream, a gel, a balm, a mascara, a foundation, or a preparation for the nails.

9. The composition according to claim 8, wherein said extract comprises 0.01% to 10% by weight dry extract of said resin.

10. A method of cosmetic treatment comprising application to the skin, the nails, the hair, or the eyelashes of a cosmetic composition as defined in claim 8.

11. The method according to claim 10 wherein said composition is a care or makeup composition.

12. The method according to claim 10, wherein said method is for delaying or lowering the effects of the aging on the skin.

13. The method according to claim 10, wherein said method is selected from a group consisting of a method for counteracting the harmful effects of free radicals on the skin, a method for treating sensitive skins and making up sensitive skins.

* * * * *